US006497881B1

(12) United States Patent
Meruelo et al.

(10) Patent No.: US 6,497,881 B1
(45) Date of Patent: *Dec. 24, 2002

(54) HIGH EFFICIENCY TISSUE SPECIFIC COMPOUND DELIVERY SYSTEM USING STREPTAVIDIN-PROTEIN A FUSION PROTEIN

(75) Inventors: Daniel Meruelo, Scarborough, NY (US); Kouichi Ohno, New York, NY (US); Brandi A. Levin, Rego Park, NY (US)

(73) Assignee: New York University, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/566,421

(22) Filed: Nov. 30, 1995

(51) Int. Cl.[7] ............................................. A61K 39/385
(52) U.S. Cl. ................................ 424/194.1; 424/130.1; 424/236.1; 424/143.1; 424/145.1; 530/387.1; 530/388.22; 530/388.23
(58) Field of Search ............................. 530/402, 387.1, 530/388.22, 388.23; 424/130.1, 143.1, 145.1, 158.1, 194.1, 236.1

(56) References Cited

U.S. PATENT DOCUMENTS 4,664,911 A * 5/1987 Uhr et al. ...................... 424/85
5,328,985 A 7/1994 Sano et al.

FOREIGN PATENT DOCUMENTS

| WO | 8911863 | * 12/1989 | |
| WO | 93/17715 | * 9/1993 | |
| WO | 94/15644 | 7/1994 | A61K/47/48 |
| WO | 97/05266 | 2/1997 | C12N/15/87 |

OTHER PUBLICATIONS

UckUn, FM et al. Science 267 (5199):886–91, 1995.*
Kim M et al J. NeuroSurg 66:161–171, 1987.*
Feshney, Culture of Animal Cells, A Manual of Basic Techniques, Alan R. Liss Inc, 1983 New York p. 4.*
Derner, Bio/Technology, 72:320, 1994.*
Gura, Science 278:1041–1042, 1997.*
Jain, Sci. Am. 271:58–65, 1994.*
Curti, Cirt. Rev. Oncol/Hematology 14:29–39, 1993.*
Hartwell, Science 278:1064–1068, 1997.*
Boado, R.J. et al. 1995. Advanced Drug Delivery Reviews 75:73–107.*
Ozawa, S. et al. 1989. Intl. J. Cancer 43(1):152–157.*
Palmer, M. et al. 1993. J. Biol. Chem. 266 (16) : 11959–11962.*
Rybak, S.M. et al. 1991. J. Biol. Chem. 266(1):21202–21207.*
Tosi, E. et al. 1991. Eur. J. Cancer 27 (Suppl 3) S57.*
Alon, R. et al. 1990 Biochem. Biophys. Res. Comm. 170:1236–41.*
Thierry Bettinger et al., Bioconjugate Chem. 1999; 10:558–561.
Melpo Christofidou–Solomidou et al., Am. J. Physiol. Lung Cell Mol. Physiol. 2000; 278:L794–L805.
Stephen Fawell et al., Proc. Natl. Acad. Sci. USA 1994; 91:664–668.
Michael Koval et al., Experimental Cell Research 1998; 242:265–273.
Christopher P. Leamon and Philip S. Low, Proc. Natl. Acad. Sci. USA 1991; 88:5572–5576.
Vladimir R. Muzykantov et al., Proc. Natl. Acad. Sci. USA 1999; 96:2379–2384.
Kouchi Ohno et al., Biochemical & Molecular Medicine 1996; 58:227–233.
Marie–Alix Poul et al., J. Mol. Biol. 2000; 301:1149–1161.
F. Wang, (Zhonghua Yi Xue Za Shi 1992; 72(7):401–4, 445–6 [Article in Chinese], English Abstract.
Adam Yu et al., DNA & Cell Biology 2000; 19:383–388.
Lianshan Zhang et al., Proc. Natl. Acad. Sci. USA 1998; 95:9184–9189.
Lambert et al., Cancer Res., 1991; 51:6236–6242.
Arteaga et al., 1994, "Epidermal Growth Factor Receptors in Human Breast Carcinoma Cells: A Potential Selective Target for Transforming Growth Factor α–Pseudomonas Exotoxin 40 Fusion Protein", Cancer Res. 54:4703–4709.
McGraw et al., 1994, "Characterization of Murine and Humanized Anti–CD33, Gelonin Immunotoxins Reactive Against Myeloid Lukemias", Cancer Immunol. 39:367–374.
Lambert et al., 1991, "An Immunotoxin Prepared With Blocked Ricin: A Natural Plant Toxin Adapted for Therapeutic Use", Cancer Res. 51:6236–6242.
Alon et al., 1993, "Cell Adhesion to streptavidin via RGD––dependent integrins", European Journal of Cell Biology 60: 1–11.
Ghetie et al., 1986, "Protein A vectorized toxins–I. Preparation and properties ofprotein A–Ricin toxin conjugates", Mol. Immunol. 23: 1373–1379.

(List continued on next page.)

Primary Examiner—Susan Ungar
Assistant Examiner—Mimh-Tam Davis
(74) Attorney, Agent, or Firm—Darby & Darby

(57) ABSTRACT

The present invention relates to methods and compositions that can be employed to introduce toxins and nucleic acids into the cytoplasm or nucleus of a eukaryotic cell, particularly a cell of a higher vertebrate. The invention particularly concerns the use of a fusion protein of streptavidin and protein A sequences to form a non-covalent complex of a toxin or nucleic acid and an antibody.

8 Claims, 9 Drawing Sheets

OTHER PUBLICATIONS

Figure 1A:
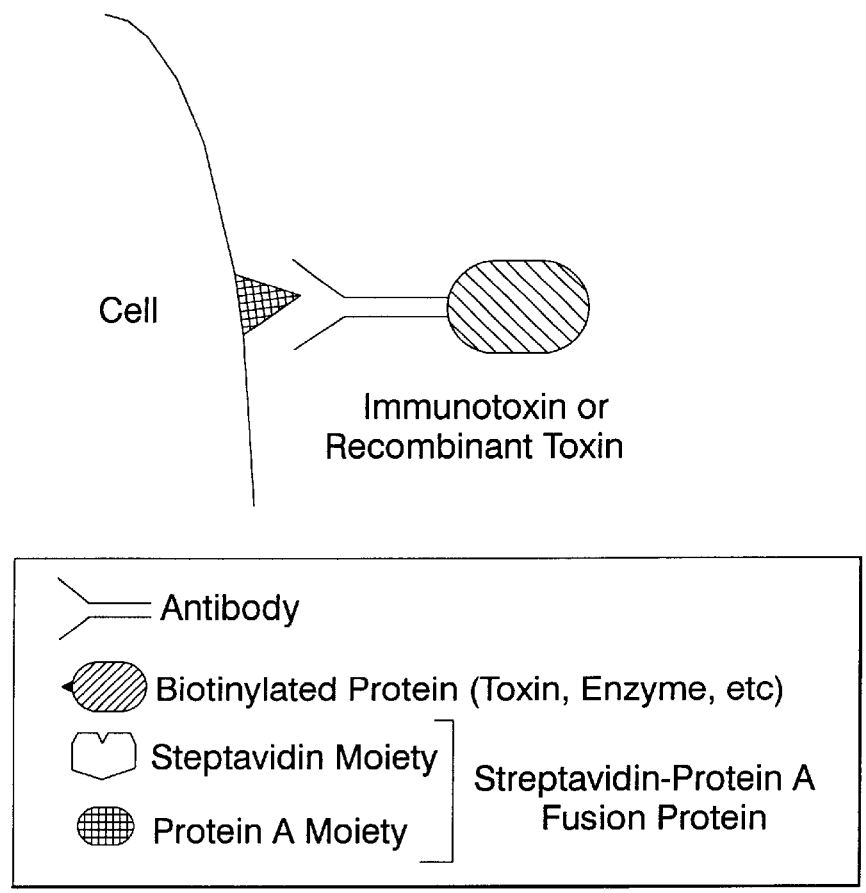
Figure 1B:
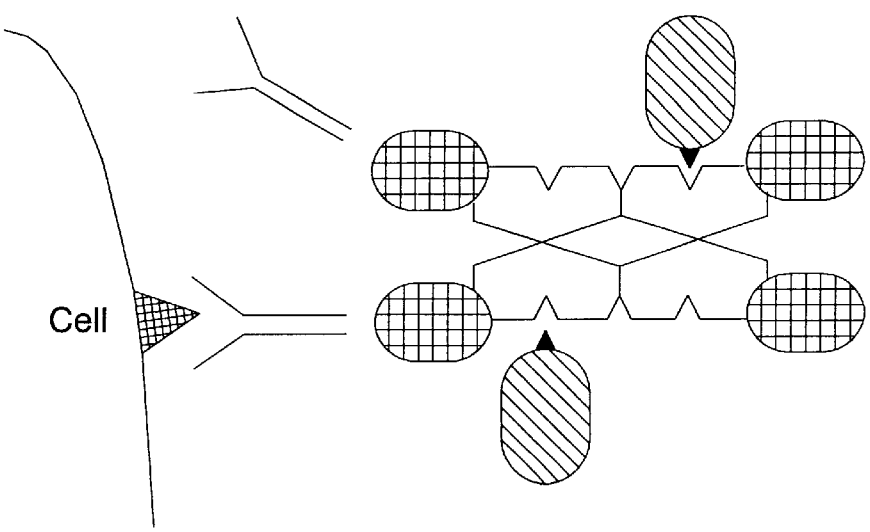
Figure 2A:
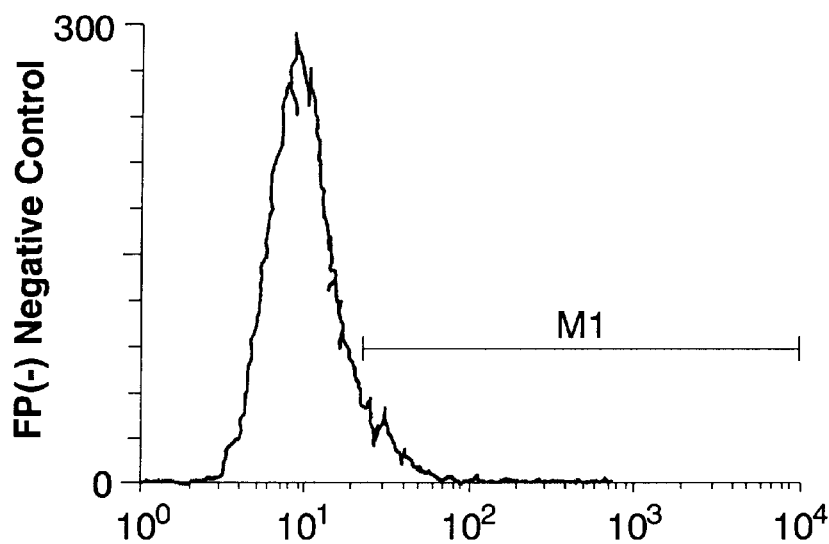
Figure 2B:
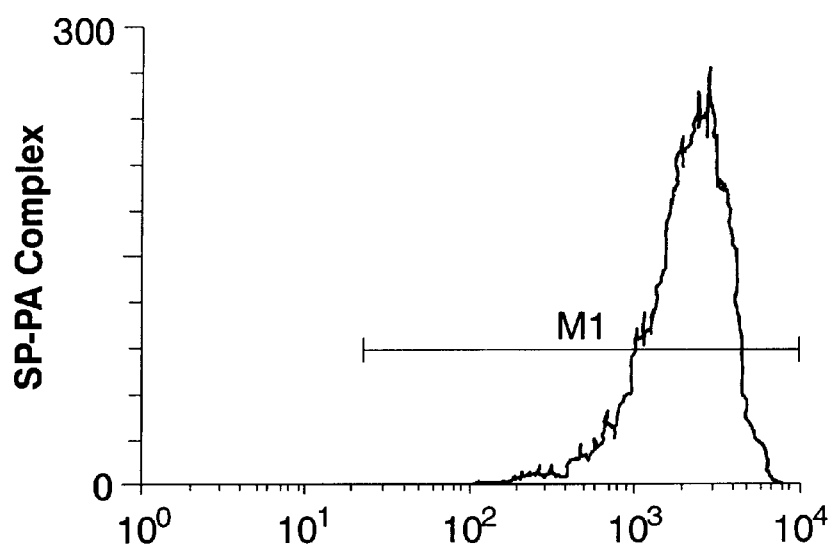
Figure 2C:
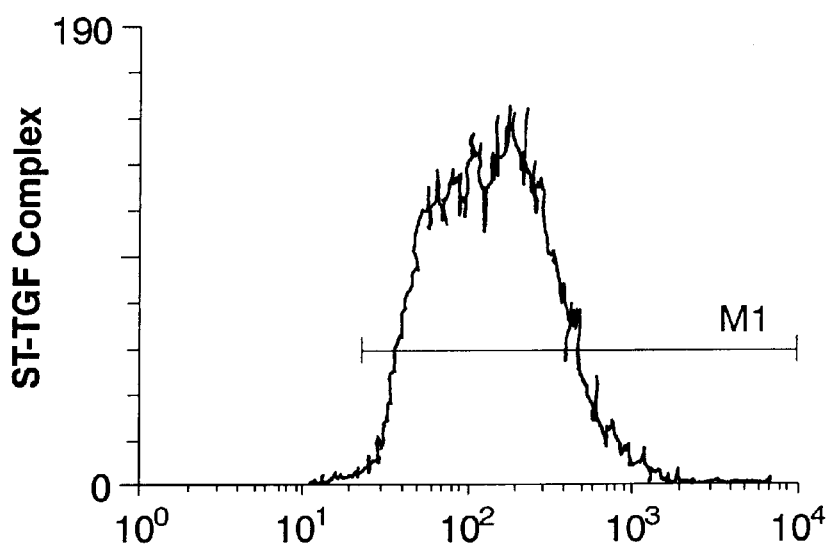
Figure 3:
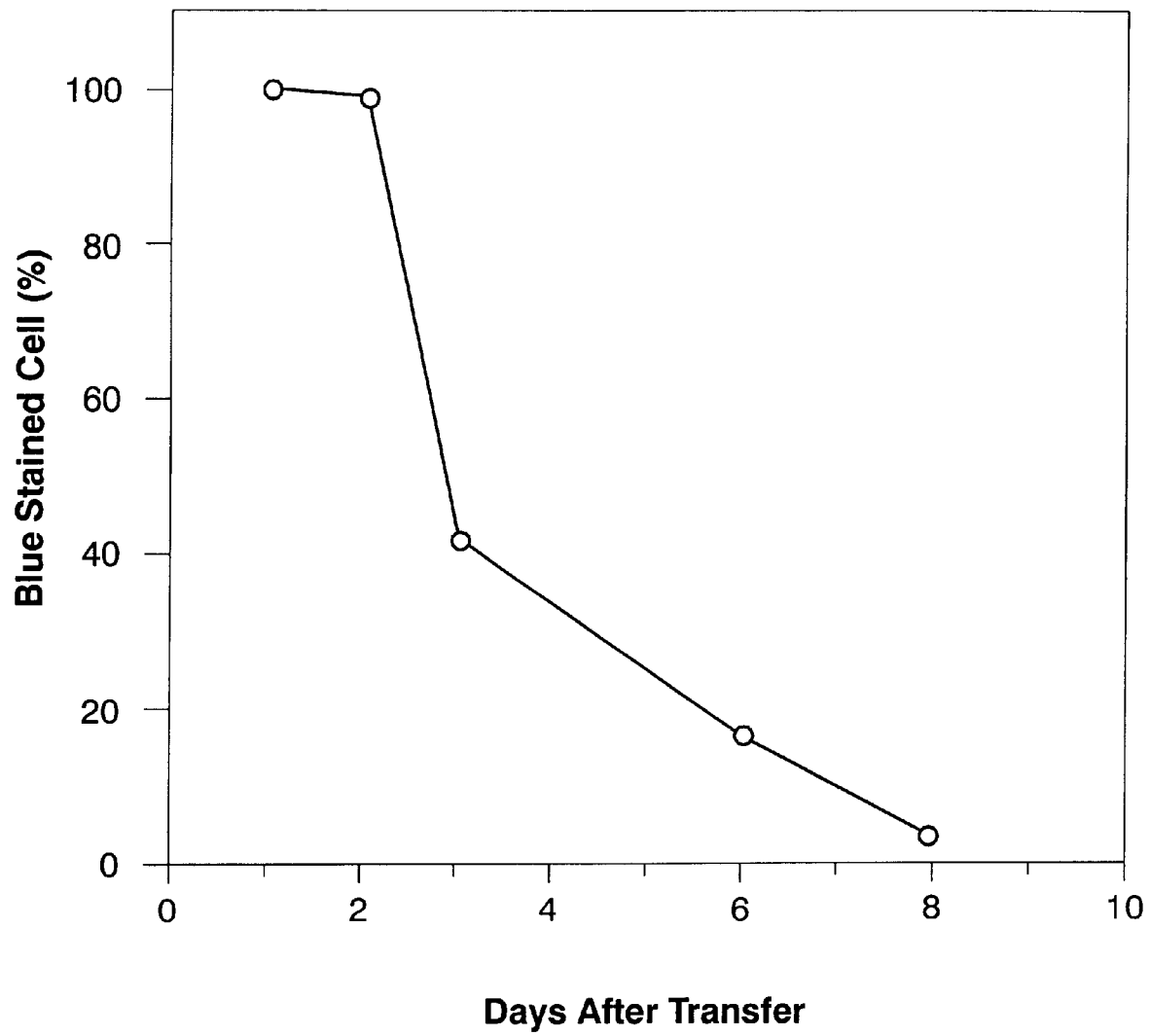
Figure 4B:
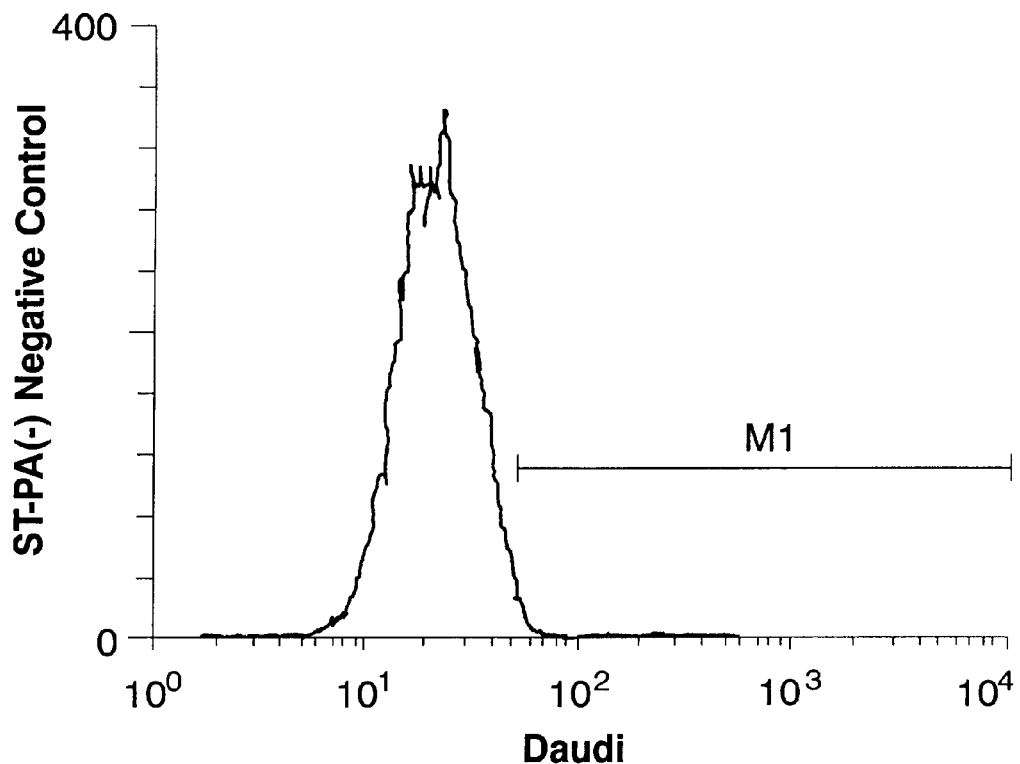
Figure 4C:
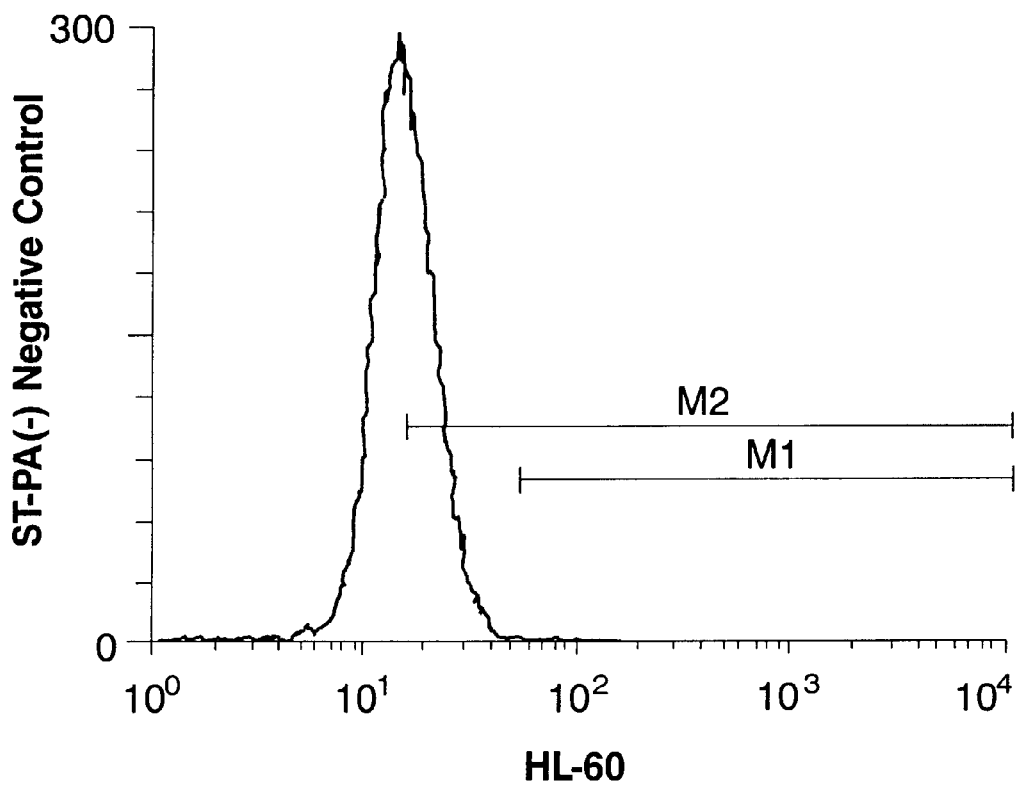
Figure 4D:
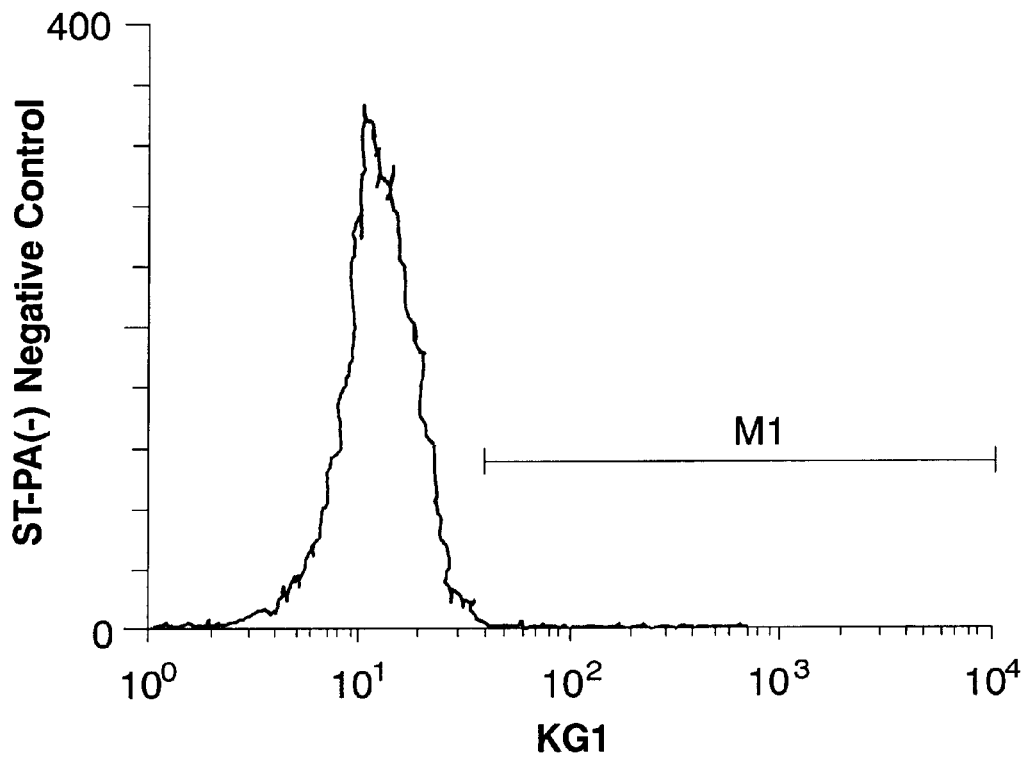
Figure 4E:
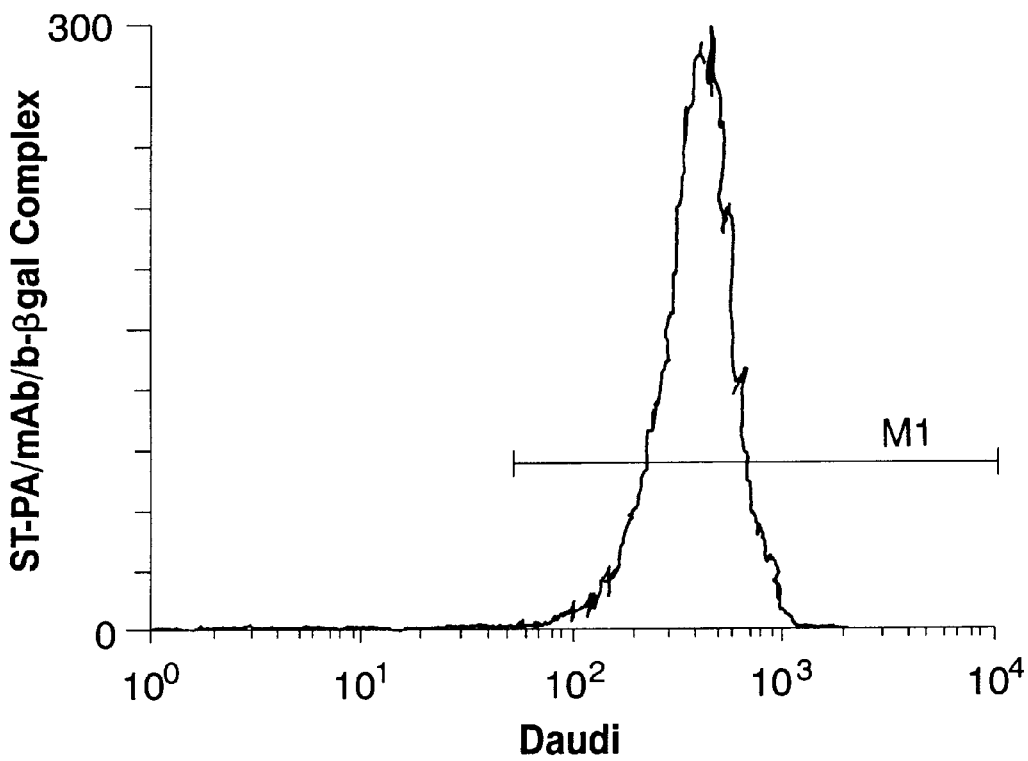
Figure 4F:
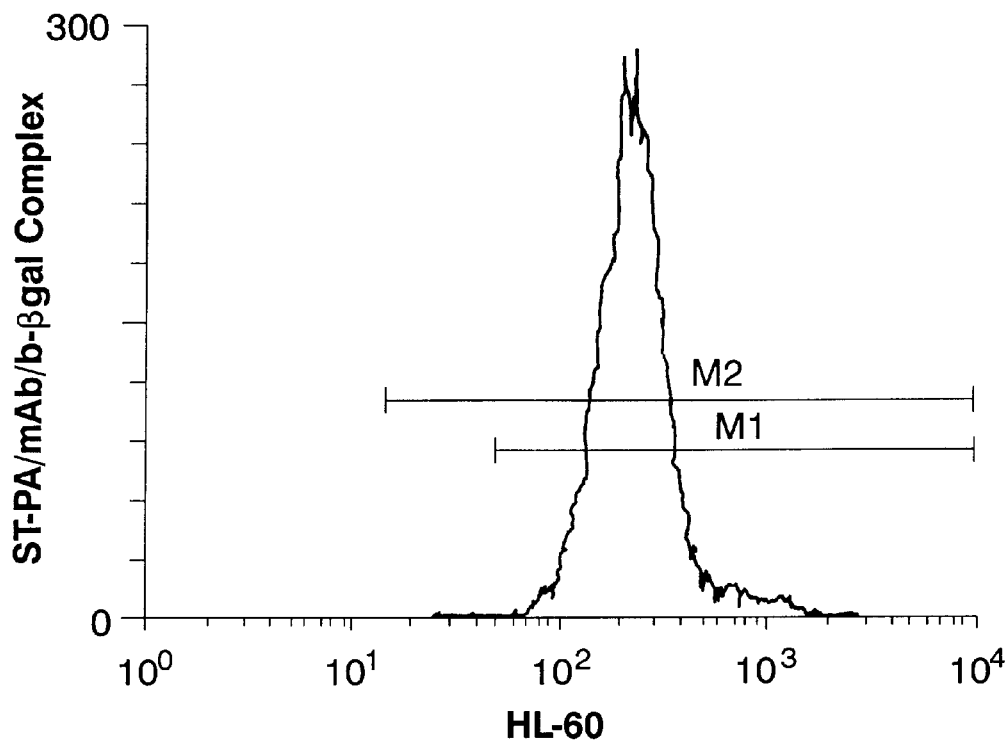
Figure 4G:
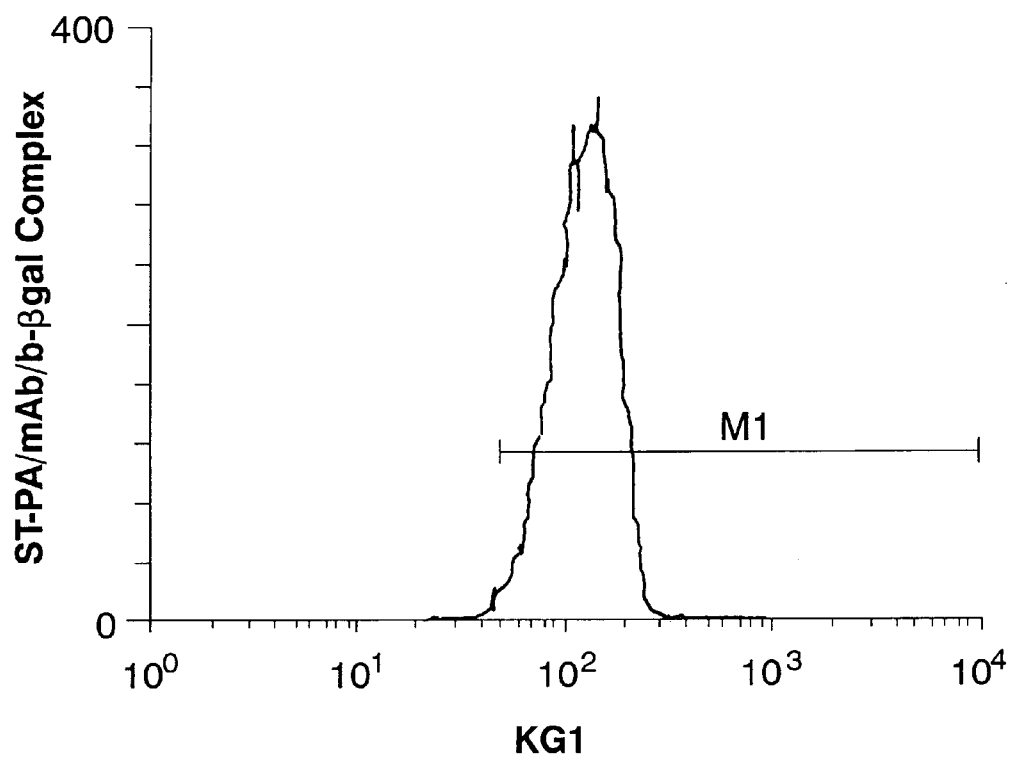
Figure 5A:
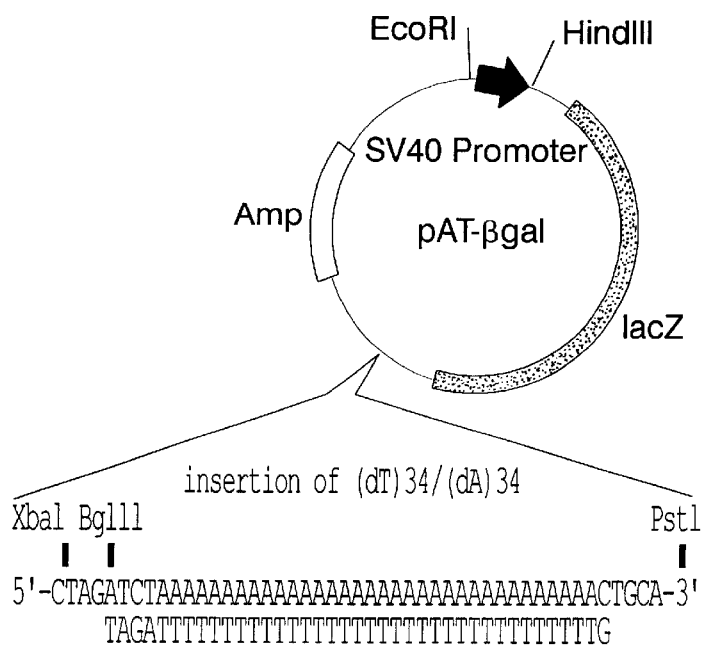
Figure 5B:
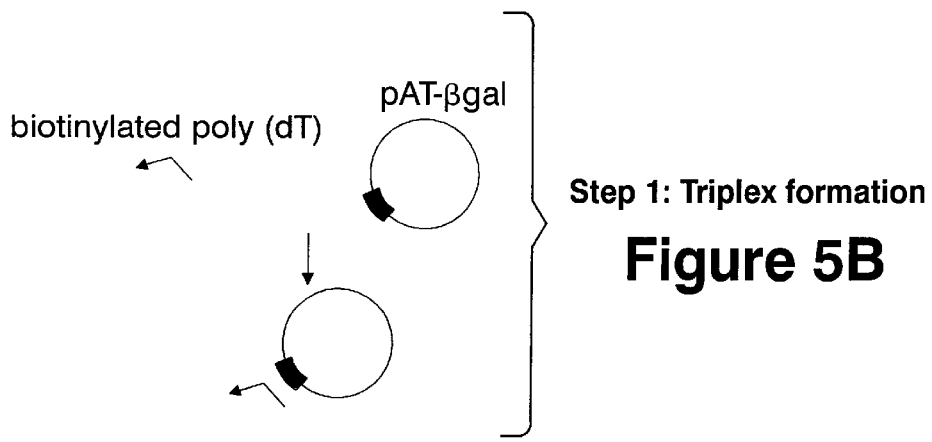
Figure 5C:
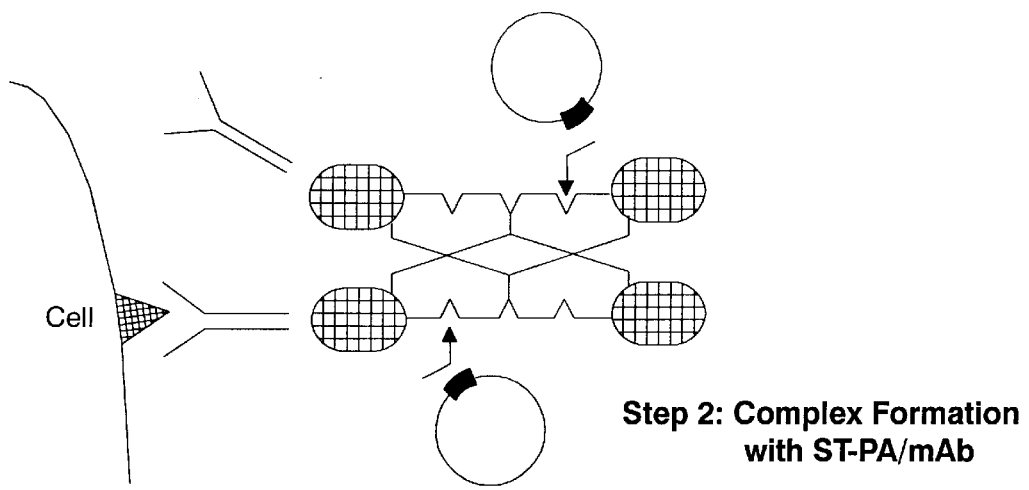
Figures 6A, 6B, 6C:
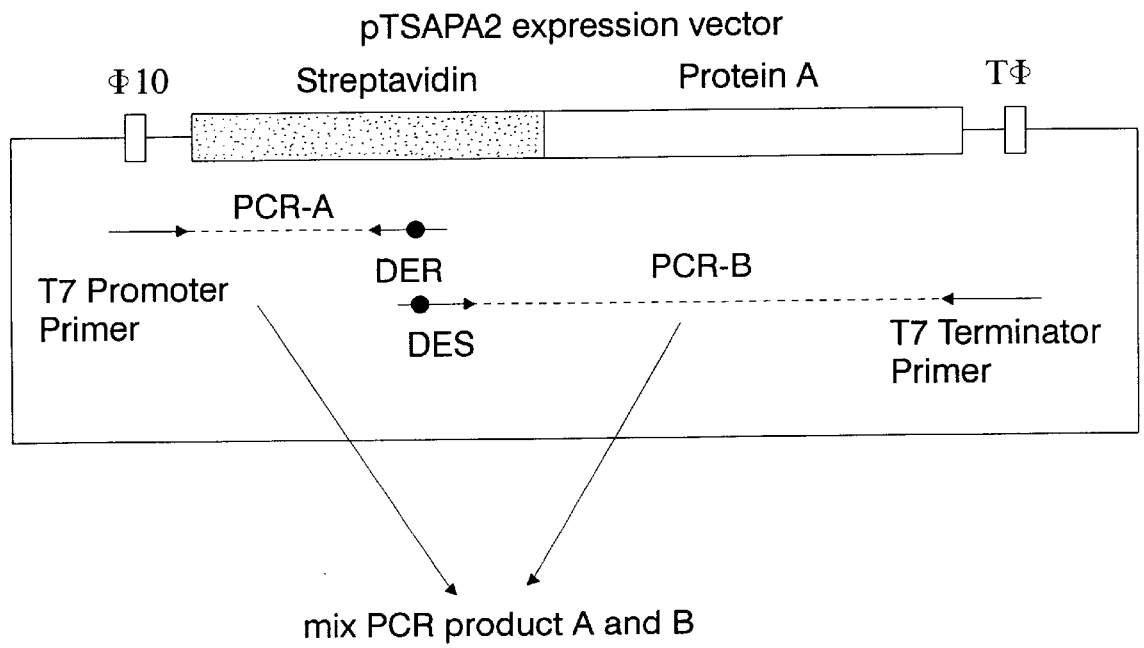

Goshorn et al., 1993, "Genetic construction, expression, and characterization of a single chain anticarcinoma antibody fused to β–lactamase", *Cancer Research 53*: 2123–2127.

Ito et al., 1992, "Sequence –specific DNA purification by triplex affinity capture", *Proc. Natl. Acad. Sci. USA 89*: 495–498.

Kiyama et al., 1994, Enrichment of Human DNAs that flank poly(dA). Poly(dT) tract bby triplex DNA formation, *J. Mol. Biol. 237*: 193–200.

Pastan and FitzGerald, 1991, Recombinant toxins for cancer treatment, *Science 254*: 1173–1177.

Sano and Cantor, 1991, "A streptavidin–protein A chimera that allows one–step production of a variety of specific antibody conjugates", *Bio/Technology 9*: 1378–1381.

Siegall et al., 1989, "Cytotoxic activities of a fusion protein comprised of TGFα and pseudomonas exotoxin", *FASEB J 3*:2647–2652.

\* cited by examiner

| Name | Cell Type | Surface Molecule |
|---|---|---|
| Daudi | Burkitt Lymphoma | HLA-DR |
| HL-60 | Promyelocytic Leukemia | CD33 |
| KG1 | Acute Myelogenous Leukemia | CD34 |

Figure 4A

Step 1: Triplex formation

Step 2: Complex Formation with ST-PA/mAb

FIBRONECTIN  YTITVYAV-TGRGDS-PASSKP        SEQ ID NO:1
STREPTAVIDIN  NAESRY-VLTGRYDSAPATDGS       SEQ ID NO:2

PRIMER   DES: 5'-<u>CGT TAC GAA</u> AGC GCC CCG-3'   SEQ ID NO:3
                    R   Y   E

PRIMER   DER: 3'-TGG <u>GCA ATG CTT</u> TCG-5'   SEQ ID NO:4

2nd PCR using T7 promoter primer and T7 terminator primer

PCR product which has a point mutation

HIGH EFFICIENCY TISSUE SPECIFIC COMPOUND DELIVERY SYSTEM USING STREPTAVIDIN-PROTEIN A FUSION PROTEIN

1. INTRODUCTION

The present invention relates to methods and compositions that can be employed to introduce toxins and nucleic acids into the cytoplasm or nucleus of a eukaryotic cell, particularly a cell of a higher vertebrate. The invention allows for the efficient and specific delivery of the toxins and nucleic acids into cells that bind an antibody. The invention particularly concerns the use of a fusion protein of streptavidin and protein A sequences to form a non-covalent complex of a toxin or nucleic acid and an antibody.

The invention provides a method of treatment of human disease by the introduction of toxins or antisense nucleotides into human cells, e.g., tumor cells, in vivo or ex vivo. The invention also provides methods of conducting biological research and methods useful in the production of biological products by introducing exogenous duplex DNA molecules into cultured cells.

2. BACKGROUND OF THE INVENTION

The selective introduction of compounds into the cytoplasm or nucleus of specific cells has been a valuable technique in biological and medical research and in medical practice. Cell specific targeting of cytotoxins has been accomplished by complexing toxins with cell binding proteins that can preferentially bind targeted cells. The cell-binding proteins of the complex can be either antibodies, particularly monoclonal antibodies, or protein ligands, e.g., /growth factors/ which recognize the corresponding surface antigens or receptor. Complexes of toxin and antibody have been termed immunotoxins.

Conventionally, the toxin and cell binding protein of the complex have been linked covalently through either chemical coupling or gene fusion. Conventional immunotoxins have been made by chemically linking a toxin component to an antibody, typically a monoclonal antibody, with a heterobifunctional cross-linking reagent that is non-specific. Accordingly, this method yields a heterogeneous product in which some toxin molecules block the antibody's ability to bind antigen by linking to the F(ab) portion of the antibody. Additionally, the coupling chemistry can partially destroy the toxins activity.

Many of the problems associated with chemical conjugation have been overcome through the generation of single-chain fusion toxins using recombinant DNA technology. However, this technology requires that a new recombinant toxin for each target cell. The biological activity of each new recombinant toxin is unpredictable.

Alternative techniques have been developed in which the cytotoxin is non-covalently linked to the antibody or ligand. One such technique exploits the specific interaction between *Staphylococcal aureus* protein A and immunoglobulins to generate antibody complexes with two specificities. According to this technique, protein A is complexed with antibodies of two different specificities: a toxin specific antibody and a cell surface specific antibody. Such complexes have been used to deliver ricin toxin into targeted cells (Laky, et al., 1986/1987, Immunology Letters 14:127–132). In a second immunotoxin targeting system, single chain antibodies are fused with streptavidin which has a strong and specific binding affinity for biotin. Using this construct, biotinylated toxin was delivered into a target cell (Dubel, et al., 1995, Journal of Immunological Methods, 178:201–209).

Recently, Sano et al. described a fusion protein consisting of streptavidin and one or two immunoglobulin G (IgG)-binding domains of protein A in *Escherichia coli*. (U.S. Pat. No. 5,328,985, issued Jul. 12, 1994, which is hereby incorporated by reference in its entirety). The streptavidin-protein A (ST-PA) fusion protein has functional biotin and IgG binding sites. Sano further described complexes of the streptavidin-protein A fusion protein, a monoclonal antibody to BSA, and biotinylated horseradish peroxidase.

Sano also described a method of labeling cells using the ST-PA fusion protein. Cells were incubated with an antibody to a cell surface antigen, Thy-1. The chimeric protein-biotinylated marker complex was subsequently added to the cell suspension. This technique was used to deliver biotinylated FITC to the surface of cells having Thy-1 antigen on their surface. However, Sano did not describe or suggest the use of the ST-PA fusion protein to deliver compounds into the cytoplasm or nucleus of specific cells.

Immunotoxins appear to enter the cell via receptor-mediated endocytosis (Pastan et al., 1986, Cell 47:1–44 and Pirker et al., 1987, Lymphokines 14:361–382). Binding of the antibody moiety of the immunotoxin complex to the surface receptor is followed by, first, clustering of the complex into coated pits and then by internalization of the complex into endosomes or receptosomes within the cell (Middlebrook et al., 1994, Microbiol. Rev., 48:199–221; Morris et al., 1985, Infect. Immun. 50:721–727; Fitzgerald et al., 1980, Cell 21:867–873). During the journey into the cell, the complex may be transported through different intracellular compartments that vary in pH and proteolytic enzyme activity before the toxins are translocated across an intracellular membrane and into the cell cytoplasm where they can cause cell death.

A second area which has been developed concerns methods for introducing nucleic acids into cells. The most widely used methods employ calcium phosphate or DEAE-dextran to promote uptake of nucleic acids. These methods appear to involve the steps of DNA attachment to the cell surface, entry into the cytoplasm by endocytosis, and subsequent transfer into the nucleus. Maniatis, Laboratory Cloning Manual, volume 2, 16.30. Depending upon the cell type, up to 20% of a population of cultured cells can take up DNA using calcium phosphate or DEAE-dextran.

Electroporation is an alternative transfection method in which an electric field is applied to open pores in the cell plasma membrane. DNA appears to enter the cell through these pores.

Liposomes have also been used to introduce nucleic acids into cells. According to this technique, artificial lipid-bilayer vesicles containing cationic and neutral lipids mediate the transfer of DNA or RNA into cells. The mechanism of liposome-mediated transfection, is not well understood, but it appears that negatively charged phosphate groups on DNA bind to the positively charged surface of the liposome, and that the residual positive charge binds to negatively charged sialic acid residues on the cell surface.

Sano did not use the complex to introduce nucleic acid into the cell. Sano et al. described DNA-antibody complexes with the ST-PA fusion protein by incorporating a single biotin molecule at one end of a linearized pUC 19 plasmid. In contrast to the methods of transfecting nucleic acids into the cell which are described above.

3. SUMMARY OF THE INVENTION

The invention relates to a method of delivering toxins or nucleic acids into specific cell types and to the complexes for the practice of the method. According to the invention, an antibody that recognizes a cell surface antigen is non-covalently bound to the antibody binding site of a ST-PA fusion protein; a biotinylated toxin or nucleic acid is bound to the biotin-binding site. In an alternative embodiment, the toxin or nucleic acid can be bound to a third biotinylated molecule, an adapter, which is bound to the biotin binding-site.

In one embodiment of the present invention, a nucleic acid is delivered into a specific cell type. The nucleic acid can be a biotinylated single stranded nucleic acid bound to the biotin binding site of the ST-PA fusion protein. In an alternative embodiment, the nucleic acid can be a duplex nucleic acid that forms a complementary triplex with a biotinylated single stranded nucleic acid, which is in turn bound to the biotin binding site.

The method of the invention relates to the steps of forming a complex between a streptavidin-protein A fusion protein; an antibody, that is specific for a cell surface protein, which undergoes endocytosis after binding with the antibody; and some targeted material e.g. a biotinylated multi-drug resistance (mdr) gene product, prodrug, toxin or nucleic acid; isolating the complex from toxin that is not bound to the biotin binding site; and exposing the target cell, to the complex so that the targeted material enters the cell.

3.1 Definitions

As used herein, toxin, refers to holotoxins, modified toxins, catalytic subunits of toxins, or any enzymes not normally present in a cell that under defined conditions cause the cell's death. A biotinylated toxin refers to a toxin that is either directly biotinylated or one that is bound to a biotinylated adapter.

The term "antibody" refers to any molecule which contains one or more functional antigen binding domains and an Fc domain that specifically binds protein A.

4. BRIEF DESCRIPTION OF THE FIGURES

FIG. 1A. Schematic representation of immunotoxin or recombinant toxin binding to the corresponding surface antigen or receptor on the cell surface.

FIG. 1B. Schematic representation of the streptavidin-protein A/biotinylated macromolecule complex binding to the corresponding surface antigen or receptor on the cell surface.

FIG. 2. Comparison of the delivery of biotin-β galactosidase into A431 cells of an ST-PA/anti-EGFR mAB/biotin-β galactosidase complex and an ST-TGF/biotin-β-galactosidase complex.

FIG. 3. Time course analysis of cell β galactosidase staining after transfer of β galactosidase into the cells.

FIG. 4A. Cell lines and cell surface molecules targeted by the ST-PA-biotin-β galactosidase-antibody complex.

FIG. 4B. Transfer of ST-PA/mAB/biotin-β galactosidase into human cells, where the mAb is specific for HLA-DR, CD33, or CD34 cell surface molecules.

FIG. 5. Schematic of the pAT-β galactosidase expression vector construct for forming triplex DNA with biotinylated poly(dT) oligonucleotide.

FIG. 6A. Amino acid homology between fibronectin (SEQ ID NO:1) and streptavidin (SEQ ID NO:2). Bold type indicates homologous residues. The RGD and RYD domain of each protein is underlined. The sequence shown for fibronectin begins at residue 1481, and the streptavidin sequence begins at residue 49.

FIG. 6B. Oligonucleotide primers DES (SEQ ID NO:3) and DER (SEQ ID NO:4) designed to modify the RYD sequence of the streptavidin gene.

FIG. 6C. Schematic of the methodology to be used in modifying the RYD sequence of streptavidin.

5. DETAILED DESCRIPTION OF THE PREFERRED EMBODIMENTS

The present invention provides a method of specific delivery of targeted material, e.g., toxins, prodrugs, mdr gene products, or nucleic acids into cells by a complex of the targeted material, an antibody specific for a cell surface antigen on the cell, which antigen is endocytosed when the cell is exposed to an effective concentration of the antibody, and a ST-PA fusion protein.

The streptavidin-protein A fusion protein (ST-PA) binds, non-covalently the cell specific antibody in the antibody binding site and the biotinylated targeted material in the biotin binding site. The manner and method by which the targeted material is biotinylated is not critical; the invention includes the use of any and all such methods and reagents.

In one embodiment, the invention provides a method for the specific destruction of cells, e.g., the destruction of tumor cells in a host or ex vivo in short term or long term culture. A toxin can be selected from the group consisting of: thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. The toxin is biotinylated and the complex of PA-ST/Ab/biotinylated toxin is formed. An effective amount of the complex can then be administered to the host or to the ex vivo culture system.

In an alternative embodiment the invention provides a method of using an antibody to a cell to introduce into the cell a cytotoxic prodrug, i.e., a non-toxic compound that is converted by an enzyme, normally present in the cell, into a cytotoxic compound. The embodiment contemplates the use of a complex of the ST-PA chimeric protein with a tumor selective monoclonal antibody and prodrug. Compounds suitable as prodrugs include by way of example glutamyl derivative of a benzoic acid mustard alkylating agent, phosphate derivatives of etoposide or mitomycin C, and phenoxyacetamide derivative of doxorubicin.

A further embodiment of the invention contemplates a complex for the delivery of single stranded nucleic acid into cells. As used herein, the term "single stranded nucleic acid" refers to both naturally and non-naturally occurring nucleic acids. The nucleic acid to be delivered can be biotinylated using any of the methods currently available, such as, random incorporation, extension reactions using DNA polymerase, and PCR with biotinylated primers. Such nucleic acids can be used to specifically destroy mRNAs to which they are complementary.

A further embodiment of the invention concerns the introduction into a cell of a duplex DNA that can integrate into the cell's genome or replicate episomally and that can be transcribed. The direct incorporation of biotin into a duplex DNA can interfere with both replication and transcription of the DNA. To overcome these problems, the duplex DNA to be delivered into the cell is modified to include a sequence that can form a region of triplex nucleic acid with a single stranded nucleic acid.

Triplex DNA formations have been described and typically consist of T-A-T and C-G-C nucleotide triads. The third strand of the triplex occupies the major groove of an A-form DNA helix and forms Hoogsteen base pairs with the homopolymeric duplex DNA. Alternatively, a triplex can be formed with duplex DNA. As used herein, the term "triplex" refers to a structure formed by Hoogsteen base pairing between a duplex DNA and a single stranded nucleic acid.

In this embodiment, the complex contains a duplex DNA Hoogsteen paired to a single stranded nucleic acid, which is biotinylated and complexed with the ST-PA/mAb complex. The duplex DNA can be a linear duplex DNA, which is suitable for recombination into the genome of a cell or, alternatively, the duplex can be a circular or supercoiled circular DNA, which can episomally replicate.

This embodiment of invention can be used under any circumstances it is desired to introduce cloned DNA into a cell, e.g., to express a product or to alter the phenotype of the cell, to investigate the function of any cloned gene.

A further embodiment of the invention comprises a complex of an antibody to a cell surface protein found on an antigen presenting cell, the ST-PA fusion protein, and a biotinylated protein of a pathological bacteria or virus, such a complex can be used to localize the antigen to antigen presenting cells and thereby enhance the immune response of CD4 positive T cells relative to that of other lymphocytes.

The complexes of the present invention can be formed by simply admixing ST-PA, a monoclonal antibody, and the biotinylated material in the appropriate ratios. The components can be mixed in any order.

The ST-PA fusion protein forms tetramers which bind up to four biotinylated molecules and four IgG molecules, which are each bivalent. Without limitation as to theory, the octovalent binding of complexes of the invention to the cell surface is believed to cause the complexes to have superior binding and internalization properties compared to other immunotoxins and immunopharmaceutical complexes.

Biotin-blocked streptavidin is capable of specifically interacting with cell surfaces through an Arg-Tyr-Asp sequence present in the protein (the "RYD site"). This site is distinct from the biotin-binding cleft of the protein and bears high homology to the RGD-containing cell binding domain of fibronectin which mediates fibronectin-cell surface interactions (Alon et al, 1993, Europ. J. Cell Biol. 60: 1–11). Studies have suggested that streptavidin acts as a close mimetic of fibronectin (Alon et al, 1993, Europ. J. Cell Biol. 60: 1–11).

The conserved RYD and RGD domains of fibronectin and streptavidin function as universal recognition sequences for interactions with many membrane-bound receptors. In one embodiment of the invention, the streptavidin component of the complex can be modified to alter the RYD site. As used herein, the term "modified RYD sequence" includes any alteration to the RYD site or flanking region which eliminates the non-biotin binding site-related interaction of streptavidin with cell surface proteins. One such modification is the replacement of aspartic acid by glutamic acid.

6. EXAMPLES

Materials and Methods

Plasmid, pTSAPA-2, described in U.S. Pat. No. 5,328,985, issued Jul. 12, 1994, carries the chimeric gene of streptavidin and protein A (region E and D). Expression and purification of the gene fusion of ST-PA was carried out according to the methods that follow.

Fusion Protein Preparation

Bacterial Strain lysogen BL21 (DE3) (pLysS) was transformed with the pTSAPA-2 streptavidin-protein A fusion expression vector. The transformed strain was grown at 37° C. in LB media supplemented with 50 µg/ml ampicillin, 34 µg/ml chloramphenicol and 0.2% glucose. When the absorbance at 600 nm of the culture was between 0.8 and 1.0 OD, 100 mM isopropyl β-D-thiogalactopoyranoside (IPTG) dissolved in water was added to a final concentration of 0.4 mM to induce the T7 RNA polymerase gene placed under the lac UV5 promoter. After the induction, the cells were incubated at 37° C. with shaking for 2 hours.

Purification of streptavidin-protein A fusion chimeric protein was carried out at 4° C. or on ice unless otherwise indicated. The culture (100 ml) of BL21 (DE3) (pLysS) (pTSAPA-2) incubated for 2 hours after the induction was centrifuged at 2,900×g for 15 min. The cell pellet was suspended in 10 ml of 2 mM EDTA, 30 mM Tris-Cl (pH 8.0), 0.1% Triton X-100, 0.5 mM PMSF to lyse the cells and the lysate was stored at −70° C. until used. To the thawed cell lysate, PMSF, leupeptin, and pepstatin A were added to final concentrations of 0.5 mM, 1 µM, and 1 µM, respectively. The lysate was then treated with 10 µg/ml of deoxyribonuclease I and 10 µg/ml ribonuclease A in the presence of 12 mM $MgSO_4$ at room temperature for 20 minutes. The mixture was centrifuged at 39,000×g for 15 minutes and the pellet was dissolved in 100 ml of 7 M guanidine hydrochloride overnight at 4° C. with stirring. After the pellet was dissolved the protein was then dialyzed against 150 mM NaCl, 50 mM Tris-Cl (pH 7.5), 0.05% Tween 20, 0.1 mM PMSF, 1 µM leupeptin, 1 µM pepstatin A, 0.02% $NaN_3$. To achieve slow removal of the guanidine hydrochloride, the dialysis bag containing the protein solution was left overnight in the dialysis solution (~1,000 ml) without stirring, followed by 3 changes of the dialysis solution and dialysis with stirring at 4° C. The dialysate as centrifuged at 39,000×g for 15 minutes, and the supernatant was applied to an IgG Sepharose 6 Fast Flow column (1.2×1.1 cm) previously washed with 5–10 bed volumes of TST Buffer. The column was then equilibrated with 2–3 bed volumes of each: 1) 0.5 M Acetic acid, pH 3.4 (pH adjusted with $NH_4CH_3COOH(NH_4Ac)$; 2) 150 mM NaCl, 50 mM Tris-Cl (pH 7.5), 0.05% Tween 20 (TST Buffer); 3) 0.5 M Acetic Acid, pH 3.4; and 4) TST. The sample was applied to the column and the unbound protein was removed by washing the column with: 1) 10 bed volumes of TST, and 2) 2 bed volumes of 5 mM $NH_4Ac$, pH 5.0. Elution was performed with 0.5 M Acetic Acid, pH 3.4. The eluate was collected in 1–2 ml fractions, and the fractions having the greatest OD at 280 were dialyzed against 1 M NaCl, 50 mM sodium carbonate (pH 11.0). The dialysate was clarified by centrifugation at 39,000×g for 15 minutes, and applied to a 2-iminobiotin agarose column (1.2×1.2 c.m) previously equilibrated with 1 M NaCl, 50 mM sodium carbonate (pH 11.0). After the unbound proteins were removed with the same solution, the bound proteins were eluted with 6 M urea, 50 mM ammonium acetate (pH 4.0). The eluted proteins were dialyzed against Tris-buffered saline [TBS; 150 mM NaCl, 20 mM Tris-Cl (pH 7.5)] containing 0.02% $NaN_3$, and the dialysate was stored at 4° C. after filtration through a 0.22 µm filter (Millex-GV, Millipore).

Formation of the ST-PA/mAb/biotinylated β-Galactosidase Complex

A mixture of ~2 µg of antibody, ~28 µg of fusion protein, and ~2 units of biotinylated β-Galactosidase was incubated at room temperature for at least 10 minutes. After this incubation, the complex is ready to use.

β-Galactosidase Staining: (X-GAL Staining)

β-Galactosidase staining of cells that adhere to the plate was performed according to Sanes, et al., 1986, EMBO J. 5: 3133–3142.

The protocol of Molecular Probes, Inc. was used to detect lacZ β-Galactosidase gene expression in cells that grow in suspension.

The above protocols were used to determine if the complex that contains the antibody coupled to the fusion protein and the biotinylated β-Galactosidase enzyme was successfully transduced into the cell of choice. If the transduction was complete, the cells were blue after overnight incubation.

2) Modification of Streptavidin Protein RYD Sequence

Biotin-blocked streptavidin binds specifically (Kd=3× $10^8$M) to cell surfaces, presumably via an RYD containing sequence that is distinct from the biotin-binding cleft of the protein.

Alternation of the RYD domain (sequence) to other amino acid residues is expected to eliminate the non-biotin related specific surface binding of a large variety of cells.

One way to modify the RYD sequence would be to change the RYD sequence to RYE. The change of RYD sequence to RYE can be achieved by introducing a point mutation using sequential PCR steps. This can be achieved by designing two primers, DES (SEQ ID NO:1) and DER (SEQ ID NO:2) (See FIG. 5) and using the pTSAPA-2 expression vector as a template of the streptavidin gene. First, PCR is carried out using two pairs of primers: T7 promoter/DER and T7 terminator/DES. Second, the two amplified DNA fragments are then purified and pooled into one sample. A second round of PCR is then performed using the pooled purified products of the first round as templates and the T7 promoter and T7 terminator primers. The mutated RYE sequence in the streptavidin gene component is confirmed through sequence analysis of the product of the second round of PCR.

3) Delivery of Biotin-β-galactosidase into A431 Cells

In order to study the ability of ST-PA to deliver compounds into a cell, the delivery of this complex was compared with that of a complex in which core streptavidin was covalently linked to the TGFα receptor. pTSA-TGFα, an expression vector for streptavidin-TGF-α (ST-TGF) was constructed by replacing the gene of protein A in pTSAPA-2 with a mature human TGF-α gene (amino acids 1–50).

To demonstrate the capability of ST-PA and ST-TGFα fusion proteins to deliver biotinylated protein into specific cells types, biotinylated β-galactosidase was complexed with the streptavidin component of the fusion protein. Delivery of β-galactosidase into A431 cells was quantitated using known staining techniques and FACS analysis.

ST-PA/biotin β-galactosidase was complexed with anti-EGFR mAb and the resulting complex was then incubated with A431 human epidermoid cells over-expressing epidermal growth factor receptor (EGFR). Alternatively, ST-TGF was mixed with biotin-β-galactosidase and the resulting complex was administered to A431 cells.

As shown in FIG. 2, ST-PA fusion protein efficiently delivered biotin-β-galactosidase into A431 cells through EGFR on its surface (positive cells >99%). The ST-TGFα fusion protein also displayed efficient delivery of biotin-β-galactosidase into A431 cells (positive cells >99%). Surprisingly, the amount of biotin-β-galactosidase delivered into each cell by the ST-TGFα fusion protein was lower than that observed in the ST-PA delivery system (the mean fluorescence activity observed was 214 and 2402, respectively).

The highly efficient delivery by ST-PA fusion protein of biotin-β-galactosidase into A431 cells may be due to the four binding sites for biotin and IgG contained on each ST-PA tetramer (FIG. 1B). In a time course experiment shown in FIG. 3, more than 99% of cells demonstrated positive staining for β-galactosidase up to 2 days after transfer of biotin-β-galactosidase into the cell.

4) Delivery of Biotin β-galactosidase into Cells Using mAbs of Different Specificity The experimental procedure applied in studying the delivery of biotin β-galactosidase into A431 cells was also used to study the delivery of the antibody/ST-PA/biotinylated β-galactosidase complex into other cell types. The study utilized antibodies that recognize several different cell surface molecules. The cell lines and cell surface molecules used in this experiment are summarized in FIG. 4A. As shown in FIG. 4B, the ST-PA/mAb complex was highly efficient (positive cells >99%) in transferring β-galactosidase into the human cell types tested by way of the HLA-DR, CD33 and CD34 molecules present on the surface of these cells.

5) pAT-β-galactosidase Expression Vector

Although biotin can be incorporated into DNA (e.g. expression plasmids), random incorporation of biotin into DNA may result in a loss of transcriptional activity. In order to retain the transcriptional activity of the DNA to be introduced into the cell, a new gene transfer system was developed which utilizes a pAT-expression vector having a poly(dA)/poly(dT) tract downstream of the expression cassette (FIG. 5). According to this transfer system, the DNA to be delivered into the cell is cloned into the expression vector. The pAT-expression vector forms triplex DNA with a biotinylated poly(dT) oligonucleotide which binds to the biotin binding site of the ST-PA fusion protein. The antibody bound to the antibody binding site of the ST-PA fusion protein targets the cells into which the DNA is to be delivered.

The protocol for triplex DNA formation and DNA transfer of the β-galactosidase gene into cells is as follows. The β-galactosidase gene is cloned into the expression cassette of the pAT-expression vector (FIG. 5). The mixture of 4 μg of pAT-β-galactosidase expression vector and 20 pmol of Biotinylated poly(dT) oligonucleotide (Promega) in TMN buffer (10 mM Tris, pH 8.0, 10 mM $MgCl_2$, 50 mMNaCl), is incubated at 37° C. for 1 hour. ST-PA fusion protein (0.5 μg) and mAB (1.0 μg) are then added to the mixture and the resulting admixture is incubated at room temperature for 30 minutes. The triplex DNA-ST-PA-mAb complex is added to the cells ($1×10^6$) and incubated at 37° C. for 48 hours. β-galactosidase activity is detected by FACS.

REFERENCES

Sano, T. and Cantor, C. R. 1991. A streptavidin-protein A chimera that allows one-step production of a variety of specific antibody conjugates. Bio/Technol. 9:1378–1381.

Pastan, I. and FitzGerald, D. 1991. Recombinant toxins for cancer treatment. Science. 254:1173–1177.

Goshorn, S. C., Svensson, H. P., Kerr, D. E., Somerville, J. E., Senter, P. D. and Fell, H. P. 1993. Genetic construction, expression, and characterization of a single chain anticarcinoma antibody fused to b-lactamase. Cancer Res. 53:2123–2127.

Siegall, C. B., Xu, Y.-H., Chaudhary, V. K., Adhya, S., FitzGerald, D. and Pastan, I. 1989. Cytotoxic activities of a fusion protein comprised of TGFα and pseudomonas exotoxin. FASEB J. 3:2647–2652.

Ghetie, M.-A., Laky, M., Moraru, I. and Ghetie, V. 1986. Protein A vectorized toxins-I. Preparation and properties of protein A-Ricin toxin conjugates. Mol.Immunol. 23:1373–1379.

Kiyama, R., Nishikawa, N. and Oishi, M. 1994. Enrichment of human DNAs that flank poly(dA). poly(dT) tract by triplex DNA formation. J. Mol. Biol. 237:193–200.

Ito, T., Smith, C. L. and Cantor, C. R. 1992. Sequence-specific DNA purification by triplex affinity capture. Proc. Natl.Acad.Sci. USA 89:495–498.

Alon R., E. Bayer, M. Wilchek, 1993, Cell Adhesion to streptavidin via RGD-dependent integrins, European Journal of Cell Biology 60: 1–11.

We claim:

1. A complex which comprises:
   a. a streptavidin-protein A fusion protein having an antibody binding site and a biotin binding site, wherein said streptavidin-protein A fusion protein forms tetramers;
   b. an antibody, bond to the antibody binding site, in which the antibody is specific for a cell protein, and in which the cell surface protein undergoes endocytosis after binding with the antibody; and
   c. a biotinylated toxin, bound to the biotin binding site, which complex is capable of transferring said toxin to a cell when contacted with the cell after forming said complex, resulting in expression of the toxin function inside the cell.

2. The complex of claim 1, in which the toxin is selected from the group consisting of:
   (a) thymidine kinase;
   (b) endonuclease;
   (c) RNAse;
   (d) alpha toxin;
   (e) ricin;
   (f) abrin;
   (g) Pseudomonas exotoxin A;
   (h) diphtheria toxin;
   (i) saporin;
   (j) momordin;
   (k) gelonin;
   (l) pokeweed antiviral protein;
   (m) alpha-sarcin; and
   (n) cholera toxin.

3. The complex of claim 1, in which there are four antibody binding sites and four biotin binding sites.

4. The complex of claim 1, in which the streptavidin component of said streptavidin-protein A fusion protein has a modified RYD sequence.

5. The complex of claim 1, which further comprises an antibody that binds transferrin receptor.

6. The complex of claim 1, wherein the antibody recognizes a surface antigen selected from the group of:
   (a) human lymphocyte antigen (HLA-DR);
   (b) cluster of differentiation (CD33);
   (c) cluster of differentiation (CD34); and
   (d) epidermal growth factor (EGF) receptor.

7. The complex of claim 1 in which the antibody is an IgG antibody.

8. A composition, comprising:
   (a) the complex of claim 1 and
   (b) a pharmaceutically acceptable carrier,
which composition is substantially free of biotinylated toxin not bound to the streptavidin-protein A fusion protein.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Tyr Thr Ile Thr Val Tyr Ala Val Thr Gly Arg Gly Asp Ser Pro Ala
1               5                  10                  15

Ser Ser Lys Pro
            20

(2) INFORMATION FOR SEQ ID NO:2:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Asn Ala Glu Ser Arg Tyr Val Leu Thr Gly Arg Tyr Asp Ser Ala Pro
1               5                  10                  15

Ala Thr Asp Gly Ser
            20

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

CGTTACGAAA GCGCCCCG                                                18

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

TGGGCAATGC TTTCG                                                   15